United States Patent [19]

Boussemaer

[11] Patent Number: 4,766,063

[45] Date of Patent: Aug. 23, 1988

[54] PROCESS AND DEVICE FOR DETECTING THE ACTIVITY OF A SUBSTANCE ON A MICRO-ORGANISM OR ON A MIXTURE OF MICRO-ORGANISMS

[75] Inventor: Jean-Pierre Boussemaer, Massieu, France

[73] Assignee: l'Air Liquide, Societe Anonyme Pour l'Etude et l'Exploitation Des Procedes Georges Claude, Paris, France

[21] Appl. No.: 681,321

[22] Filed: Dec. 13, 1984

[30] Foreign Application Priority Data

Dec. 14, 1983 [FR] France .................. 83 20014

[51] Int. Cl.⁴ .......................... C12Q 1/70; C12Q 1/18; C12Q 1/20
[52] U.S. Cl. .......................... 435/5; 435/32; 435/33
[58] Field of Search .......... 435/5, 32, 33, 292, 435/293, 294, 299, 300, 301, 810; 436/23, 63

[56] References Cited

U.S. PATENT DOCUMENTS

| | | |
|---|---|---|
| 2,956,931 | 10/1960 | Goldberg .................. 435/5 |
| 3,843,456 | 10/1974 | Haden . |
| 4,073,694 | 2/1978 | Buda et al. .................. 435/32 X |
| 4,090,920 | 5/1978 | Studer, Jr. .................. 435/33 X |
| 4,153,512 | 8/1979 | Messner . |
| 4,154,795 | 5/1979 | Thorne .................. 435/300 X |
| 4,218,534 | 8/1980 | La Belle et al. .................. 435/5 |
| 4,284,725 | 8/1981 | Fennel .................. 435/301 |
| 4,599,314 | 7/1986 | Shami .................. 435/300 X |

FOREIGN PATENT DOCUMENTS 0005891 12/1979 European Pat. Off. .
1494358 12/1977 United Kingdom .

OTHER PUBLICATIONS

Staining Procedures, G. Clark (editor), Fourth Edition, Williams & Wilkins, Baltimore, 1981, pp. 275-276, 281-282, 446-447.
Chemical Abstracts, vol. 89, 1978, Abstract No. 20104c, Kruszewska et al.
Biological Abstracts, vol. 71, 1981, Abstract No. 29531.

*Primary Examiner*—Robert J. Warden
*Assistant Examiner*—Randall E. Deck
*Attorney, Agent, or Firm*—Browdy and Neimark

[57] ABSTRACT

The presence of fermentation inhibiting activity in a sample is determined by contacting the sample with bacterial strains and detecting the inhibition of the activity of the strains. A carrier (1) carrying microtitration cups arranged in four rows of cups (8) is provided. The cups of the same row contain a lyophilisate comprising a given bacterial strain. Each sample to be tested, effected in a tube (3), is diluted in a tube (4) containing a culture medium and bromocresol purple and then poured into the cups of a given column by means of an automatic pipette and cones (5). After incubation, a drop of janus green reagent in tube (6) is introduced in each cup and, after a new incubation, the number of cups which have produced a change in color indicates the degree of contamination of the mixture. The process may be applied in the determination of bacteriophages present in cheese-making vats.

5 Claims, 2 Drawing Sheets

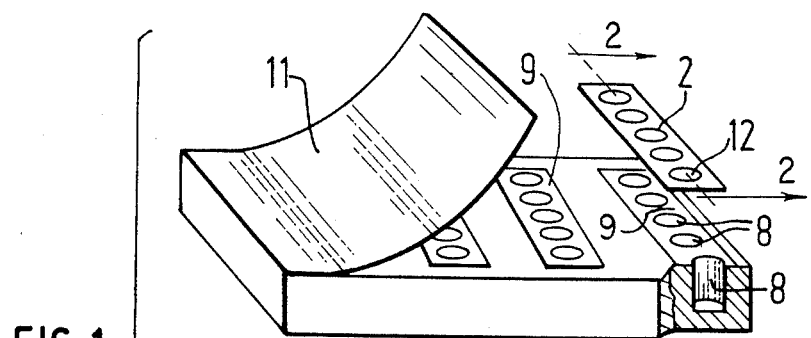
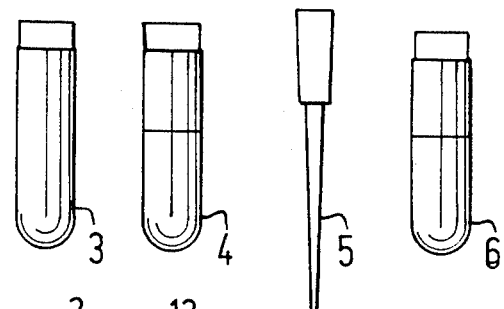
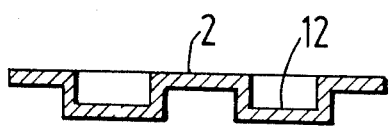
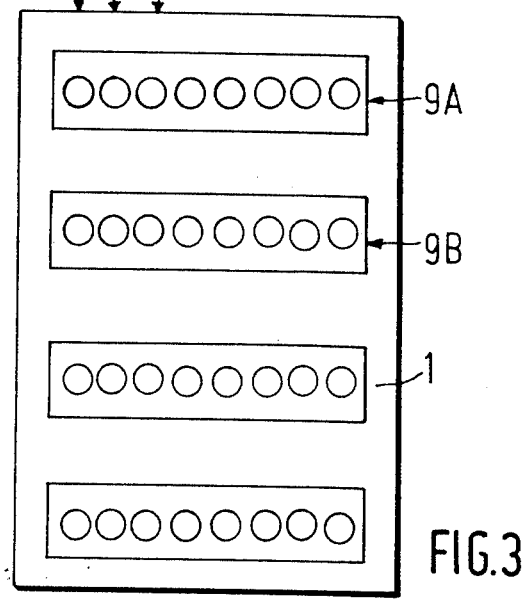
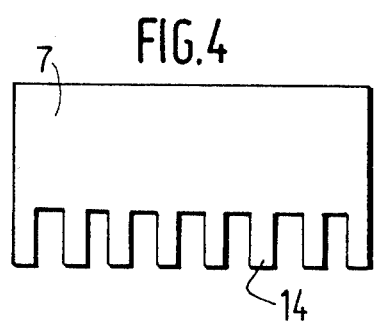

PROCESS AND DEVICE FOR DETECTING THE ACTIVITY OF A SUBSTANCE ON A MICRO-ORGANISM OR ON A MIXTURE OF MICRO-ORGANISMS

The present invention relates to a process for detecting the activity of a substance on a micro-organism or on a mixture of a plurality of micro-organisms, and to a device for carrying out that process. The invention is in particular applicable to the detection of bacteriophages in cheese-making.

In cheese-making, the milk is fermented in vats by means of a yeast produced from a mixture of a certain number of bacterial strains. In the course of time there are developed in the vats micro-organisms termed bacteriophages, or more simply phages. The growth of these phages involves the growth of lactic bacteria and is considerably more rapid than that of the latter. The phages are more or less specific to the lactic bacteria employed. Beyond a certain concentration of a given type of phage in the vat, the corresponding bacteria are destroyed to a sufficiently great extent so as to no longer produce the expected fermentation. The problem in cheese-making occurs when a sufficient proportion of the strains is contaminated.

The activity of the lactic bacteria may also decrease for other reasons. In particular, it may be stopped by the presence of inhibiting substances, which are in the milk employed or produced by the bacteria themselves, or by antibiotics present in the air.

Thus cheese-makers require a test which permits the reliable determination of the presence of either of these harmful factors.

An object of the invention is to provide a very sensitive reliable test which is extremely simple to use, particularly in cheese-making, where it permits the obtainment of a veritable scale of phage contamination of the mixtures of bacterial strains.

The invention therefore provides a process for detecting the activity of a substance on a micro-organism which comprises the following series of steps:

(a) Preparing in a vessel a lyophilized medium containing the micro-organism and a part of a culture medium of this micro-organism.

(b) Preparing a solution containing the complement of said culture medium.

(c) Adding said substance to said solution.

(d) Pouring the liquid thus obtained into the vessel.

(e) Incubating the vessel.

(f) Subjecting the vessel to a test for determining the presence of the micro-organism.

In a particularly interesting manner of carrying out the invention, the process of the invention is applied to the determination of the activity of said substance on x micro-organisms. In this case, the step (a) mentioned above is replaced by the following step (a1):

(a1) Preparing in each of the x vessels a lyophilized medium containing a respective micro-organism of the mixture and a part of a culture medium of all of the micro-organisms; and applying each of the steps (d), (e) and (f) to each of the vessels.

Another object of the invention is to provide a device or kit for carrying out the last-mentioned process. This device comprises:

a carrier unit for microtitration cups comprising x rows of y cups, each row containing a lyophilized medium which itself contains a respective micro-organism of said mixture;

4(y−1) sterile sampling tubes, and 4 y dilution tubes containing said solution.

In an advantageous embodiment, the device according to the invention further comprises a stirring comb whose teeth are adapted to penetrate simultaneously into all the cups of the same row or of the same column.

As the cups or cavities must be closed or opened with a stopper several times, according to another advantageous feature of the invention, the rows of cups are provided with a closing system consisting of a sheet from which downwardly project blind spigots in a number equal to the number of cups and adapted to be a force fit in these cups.

An example of a manner of carrying out the invention will now be described with reference to the accompanying drawings, in which:

FIG. 1 is a diagrammatic view of a device according to the invention for the studying of a mixture of lactic bacteria employed in cheese-making;

FIG. 2 is a partial sectional view taken on line II—II of FIG. 1;

FIG. 3 is a plan view of the microtitration plate of FIG. 1;

FIG. 4 is a view of an accessory which may be used with the device of FIG. 1.

Figure 5:
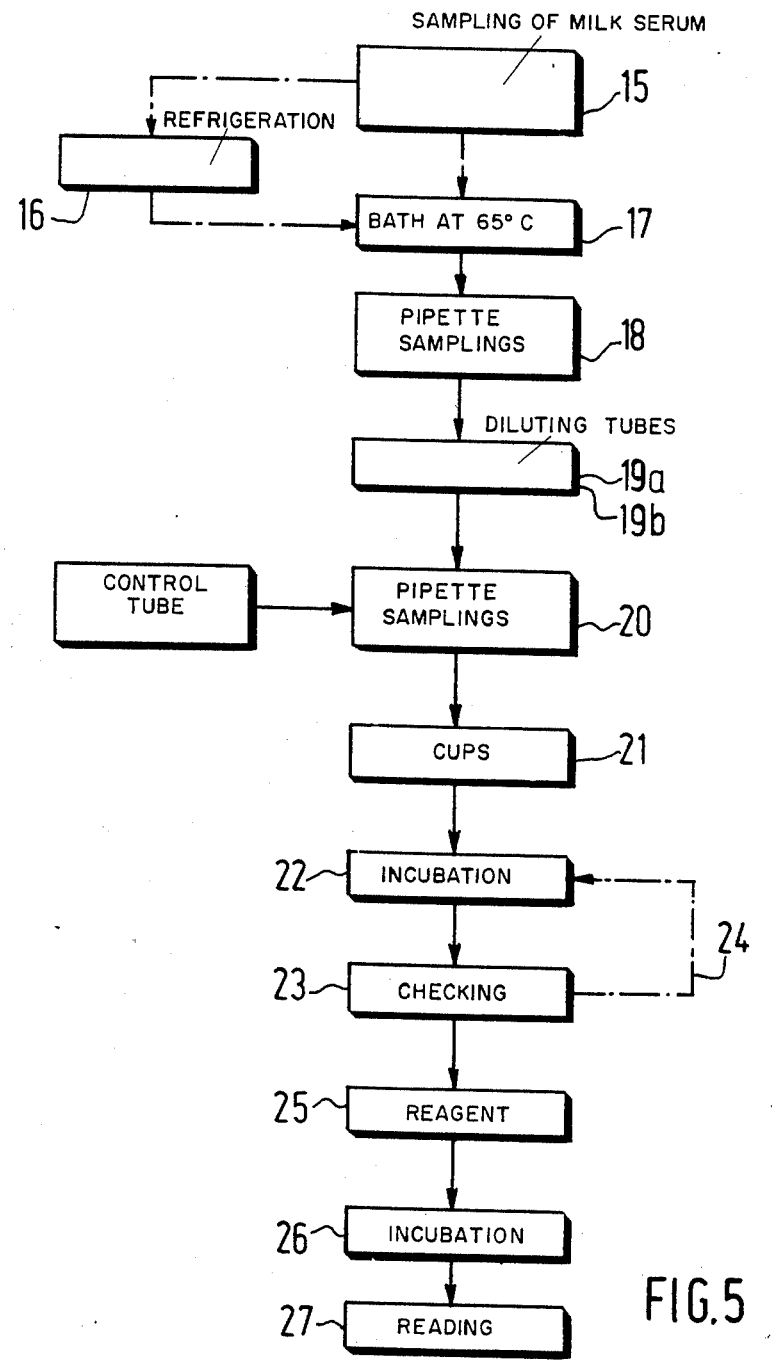
FIG. 5 is a diagram illustrating the various steps of the process carried out with the device of FIGS. 1 to 4.

The process which will now be described is applied to cheese-making. It permits the determination at any moment of the degree of contamination of the mixture of bacterial strains in the course of fermentation in a vat, in the case where this mixture consists of a group of well-determined strains. There will first be described, with reference to FIGS. 1 to 4, the device or kit permitting this determination.

This device mainly comprises: a carrier having three or four rows of microtitration cups or cavities 1 provided with a cover 2; a series of twenty-eight sampling tubes 3; a series of thirty-two dilution tubes 4; a series of commercially available sampling cones 5 adapted to act as interchangeable end members for an automatic pipette (not shown); and a reagent tube 6. There may be added to these elements a stirring comb 7 shown in FIG. 4. A single tube 3, a single tube 4 and a single cone 5 have been shown in FIG. 1 for reasons of clarity. Elements 1 to 4 are sterile. The cup carrier 1 comprises a sheet of thermoformable plastics material (P.V.C.) having a parallel-sided shape and including in its upper side four receiving portions, each receiving portion being capable of receiving a row of eight cups. The eight cups of a given row contain the same strain. Consequently, there are as many rows as there are strains in the mixture. An empty receiving portion identical to the preceding receiving portion is adapted to receive a row of cups so as to collectively constitute a carrier containing the strains of the mixture to be tested. Assuming that the carrier is oriented as viewed in plan in FIG. 3 with its large sides vertical, each horizontal row carrying the reference characters 9A, 9B, . . . is assigned to a given strain A, B, . . . of the mixture. The first column 10a, that is that on the left in the illustrated embodiment, constitutes a control column and each of the seven other colmuns 10b, 10c, . . . is assigned to a sample. The carrier thus permits the testing of one to seven samples with a mixture containing one to four strains A, B, . . .

Each cup 8 contains a strain preserved in the lyophilized form. More precisely, this strain is incorporated in a lyophilisate forming, on one hand, a protector of the bacteria as concerns the lyophilization and, on the other hand, a part of a culture medium of the strain. By way of an example, this lyophilisate may be constituted as follows:

| | |
|---|---|
| saccharose | 54 g |
| glycerophosphate | 75 g |
| Na glutamate | 20 g |
| yeast extract | 30 g |
| sodium chloride | 12 g |
| calcium chloride | 2.25 g |
| sodium acetate | 4.5 g |
| magnesium sulphate | 0.6 g |
| powdered milk | 62.5 g |
| $H_2O$ to make up | 1000 ml |

The strain is incorporated in this medium before lyophilization in a proportion which varies from 1 to 10% depending on the strain, in the form of a culture grown for sixteen hours in sterilized peptoned milk coagulated by the strain.

The lyophilization is carried out directly in the carriers. When the lyophilization has ended, the cover 2, which will be described in more detail hereinunder, is placed in position on the rows of cups and the carriers are sealed by metalloplastic sheets 11 (which are in laminations comprising an outer metal layer and an inner layer of plastics material thermowelded to the carrier) and maintained at +4° C.

The cover or lid 2 is formed by a sheet of flexible and transparent plastics material having roughly the same dimensions as a row of cups 9. Formed in this sheet are eight blind substantially cylindrical spigots 12 which project downwardly and have the same arrangement and substantially the same diameter as the cups 8. When the lyophilization of the carrier 1 has ended, the cups 8 are closed in a sealed manner by firmly applying the cover 2 on the row of cups 9, each spigot 12 fitting, with a slight force applied, in the corresponding cup.

The plastics material of the cover 2, as the material of the carrier 1, must of course possess physical and chemical properties adapted to the handled bodies and to the temperatures to which it is subjected, and in particular to a cold condition of −30° C., for a low cost. For example, the carrier may be made from crystal polystyrene and the cover 2 from polystyrene.

Each of the eight dilution tubes 4 contains 3 ml of a liquid medium for, on one hand, rehydrating the lyophilisate contained in the cups 8 of a column 10a, 10b, . . . , and,on the other hand, the diultion of a sample taken with a tube 3, and the complementation of the culture medium of the lyophilisate. This medium has the following composition:

| | |
|---|---|
| yeast extract | 20 g |
| lactose | 30 g |
| $H_2O$ to make up | 1 liter |
| BCP (bromocresolpurple) | 0.02 g |

This medium has a pH of 6.5 and is sterilized at 120° C. for twenty minutes. BCP is an indicator of pH and its colour is purple at a pH higher than about 5 and yellow at pH lower than this value.

The tubes 6 contain a reagent enabling the results of the test to be read. This reagent is a sterile solution of "janus green" and 20 μl thereof are poured into each cup, the janus green being diluted at 0.25 g/l. This reagent has the property of changing to a pink colour in the presence of lactic bacteria.

The comb 7 is a piece of a sheet of plastics material having a generally semi-disc shape. On the diameter of this semi-disc there project eight rectangular teeth 14 whose width is less than the diameter of the cups 8.

The device just described is employed in the following manner, illustrated in FIG. 5. The study concerns a milk treated in a cheese-dairy with a yeast formed, for example, with a mixture of eight strains A, B, . . . There are analyzed on the eight strains the four principal strains respectively preserved in the eight rows 9A, 9B, . . . of this carrier.

For reasons of economy, it is desirable to effect the maximum possible samplings (reference 15 in FIG. 5), i.e. seven samplings. The number of samples per day depends on the technological parameters of the cheese-dairy (volume of treated milk, number of vats, etc.) and the objects to be obtained (checking contamination, explanation of an ascertained incident, regular inspection, etc.). If this number is less than 7, the samples are preserved in a refrigerator or a deep freezer, as illustrated at 16 in FIG. 5. The samples are formed by a starting pasteurized milk or by serum of a vat in the process of fermentation.

On the day of the test, a thermostat-control bath is set to 65° C. The samples of serum, after having possibly been brought to ambient temperature, are placed for seven minutes in this thermostat-controlled bath (reference 17 in FIG. 5).

This operation eliminates both the lactic bateria and a notable part of the inhibiting substances without destroying the bacteriophages.

As soon as the product leaves the bath, 170 μl of each sample is drawn off by means of a pipette provided with a piston and termed "automatic pipette" which is preadjusted to this volume and provided with a cone (reference 18). These 170 μl are poured into tube water 4 (reference 19) which is agitated. Thus, seven tubes 4 receive a measured amount of a respective sample while the eighth tube 4, which is a control tube, does not received a sample.

All the following operations are carried out close to a flame (bunsen burner) so as to ensure sterility of the handling.

The rows of cup are disengaged from each of the three or four receiving portions. The three or four rows of cups thus disengaged are disposed in an empty carrier. The cover of each row is withdrawn. The following step (reference 20) comprises taking from each tube 4 by means of the same automatic pipette provided with a new cone 5, which is changed for each tube, measured amounts of 170 μl which are poured into the cups 8 (reference 21). More precisely, each cup 8 of the column 10a receives 170 μl coming from the control tube 4, each cup of the second column 10b receives 170 μl coming from the tube 4 which contains the first sample, etc. During this operation, care is taken not to touch the edge of the cups or the lyophilisates with the distribution cone so as to avoid contamination.

After having distributed in this way all the samples, the covers 2 are placed back in their initial position. After a few minutes, the carrier is agitated in the horizontal direction while avoiding contact between the liquid and the cover, and then it is incubated at 30° C. for 16 to 20 hours (reference 22). This period is so determined as to enable the strains contained in the first column 10a to lower the pH below 5. Therefore it is checked (reference 23) that all the cups of the column 10a have become yellow, otherwise the incubation is continued a short time (reference 24).

Then 20 μl of reagent of the tube 6 are then poured into each cup and the latter are agitated (reference 25). For this purpose, the carrier may be agitated horizontally, as before, but as the microbiological phenomena have ended at this stage and any risk of intercontamination is consequently avoided, it is convenient to employ the comb 14 which permits stirring in a single movement all the cups of a column and then all the cups of the following column, etc. Then the carrier provided with the covers 2 is again incubated at 30° C. (reference 26) for about 45 minutes to 1 hour so as to cause the janus green to react.

It merely remains to withdraw the carrier from the stove, to withdraw the covers 2 and to carry out the reading (reference 27). Three cases may be met with which result from the following considerations in respect of each strain of the mixture:

if the milk samples result in a pink colour, this signifies that the milk employed has not prevented the activity of the strain. Consequently it does not contain an inhibiting substance or an antibiotic harmful to the fermentation by this strain;

if the milk samples result in a green colour, this milk contains inhibitors and antibiotics. This is also found in the vat so that the strain cannot act, even in the absence of phages.

If the serum samples result in a green colour, there are in the vat either inhibitors and/or antibiotics coming from the milk, or phages.

Consequently, in taking both samples of milk and samples of serum, the following conclusions may be drawn:

| Milk | Serum | Interpretation |
|------|-------|----------------|
| pink | pink  | normal |
| green | green | inhibitor or antibiotic in the milk |
| pink | green | bacteriophages |

Assuming that the milk is devoid of inhibitor and antibiotic, the proportion of green cups relative to all of the cups gives the proportion of strains of the mixture contaminated by the bacteriophages. It can usually be considered that, up to 40% of green cups, there is no risk in using this mixture 2 to 3 days. On the other hand, beyond this proportion, it is essential to change the mixture to maintain production.

This test, carried out on pure strains (i.e. isolated strains) of the employed mixtures, indicates in a reliable manner the degree of contamination of these mixtures. Owing to its arrangement in the form of an inexpensive kit, it is simple to use. The preservation of the strains in the lyophilized form at well-defined concentrations avoids any operation of bacterial culture or subculture. The culture medium employed ensures a very good growth of the strains and of the phages and a very good protection of the lyophilized strains. Further, the janus green has a very distinct change of colour which facilitates the interpretation of the results.

A similar test may be applicable in other cases of productions involving bacterial fermentation, for example in the production of glutamate or antibiotics. It may also be suitable for the lysotypage of strains, i.e. for testing a series of bacterial strains on a collection of phages contained in the carrier in the proportion of one type of phage per row. This technique would provide a rapid and convenient process for testing the resistance of the strains and even enable strains to be characterized in a more certain and more convenient manner than the biochemical characters employed at the present time.

What is claimed is:

1. A process for determining the fermentation-inhibiting activity of serum used in the production of cheese from milk by lactic acid-producing bacteria, comprising the steps of:
   (a) preparing, in a vessel, a lyophilized medium containing a pure culture of a lactic acid-producing bacteria used in a serum for the production of cheese and a first culture medium for said bacteria;
   (b) preparing a solution comprising bromocresol purple and a second culture medium for said bacteria;
   (c) heating a sample of said serum at a temperature and time sufficient to destroy bacteria and inhibitory substances therein without killing phage;
   (d) adding said sample from step (c) to said solution from step (b) to obtain a liquid;
   (e) pouring said liquid into said vessel;
   (f) incubating said vessel with said liquid therein for a sufficient time to permit said lactic acid-producing bacteria to reduce the pH within said vessel to a value below 5 when no inhibiting activity is present;
   (g) adding janus green to the incubated vessel thus turning the color of the contents of said vessel green;
   further incubating said vessel, with said janus green therein, for a time sufficient for the contents of said vessel to turn pink when active lactic-acid producing bacteria are present;
   (h) observing the color of the contents of the vessel obtained according to step (g) and thereby determining the presence of inhibiting activity, wherein a green color is positive for the presence of inhibitory activity in said sample and a pink color is negative for the same.

2. The process of claim 1, wherein said serum comprises one or more strains of lactic-acid producing bacteria, preparing at least one of said vessels as per step (a) for each strain of lactic acid-producing bacteria in said serum, a pure culture of each of said one or more strains being contained with a different one of said vessels, further comprising:
   repeating steps (c)-(h) upon each said vessel prepared as per step (a).

3. The process of claim 2, further comprising the steps of:
   (o) for each said strain, preparing a plurality of vessels containing said strain according to step; and
   (p) for each of said vessels prepared according to step (o), performing steps (c)-(h).

4. The process of claim 1, further comprising:
   preparing a control vessel comprising a lyophilized medium containing a pure culture of said lactic acid producing bacteria and said first culture medium for said bacteria;
   adding the solution of step (b) to said control vessel;
   incubating said control vessel containing the solution from step (b) while simultaneously performing step (f) upon said vessel prepared as per steps (a)-(e), under the same incubation conditions, until said bromocresol purple in said control vessel turns yellow, then terminating step (f).

5. The process of claim 1, wherein the fermentation-inhibiting activity of milk to be fermented is also determined, further comprising the steps of:
(i) preparing in a second vessel, a lyophilized medium containing a pure culture of said lactic acid-producing bacteria and said first culture medium for said bacteria;
(j) preparing a second solution which is the same as that in step (b);
(k) adding a sample of milk to be fermented to said second solution from step (j) to obtain a second liquid;
(l) incubating said second vessel with said second liquid therein for a time sufficient to permit said lactic acid-producing bacteria to reduce the pH within said vessel to a value below 5 when no inhibiting activity is present in the milk;
(m) adding janus green to the second incubated vessel thus turning the color of the contents of said second vessel green;
further incubating said second vessel, with said janus green therein, for a time sufficient for the contents of said second vessel to turn pink when active lactic-acid producing bacteria are present;
(n) observing the color of the contents of said second vessel and determining the presence of inhibiting activity in said milk, wherein a green color is positive for the presence of inhibitory activity in said sample of milk and a pink color is negative.

* * * * *